United States Patent
Van Der Bruggen et al.

(10) Patent No.: US 7,488,793 B2
(45) Date of Patent: Feb. 10, 2009

(54) **ISOLATED PEPTIDE WHICH BINDS TO HLA-CW*07 AND USES THEREOF**

(75) Inventors: Pierre Van Der Bruggen, Brussels (BE); Thierry Boon Falleur, Brussels (BE); Karine Breckpot, Brussels (BE); Kris Thielemans, Brussels (BE)

(73) Assignee: Ludwig Institute For Cancer Research, New York, NY (US)

( * ) Notice: Subject to any disclaimer, the term of this patent is extended or adjusted under 35 U.S.C. 154(b) by 441 days.

(21) Appl. No.: 10/941,150

(22) Filed: Sep. 15, 2004

(65) Prior Publication Data

US 2005/0226881 A1  Oct. 13, 2005

Related U.S. Application Data

(60) Provisional application No. 60/504,874, filed on Sep. 22, 2003.

(51) Int. Cl.
| | |
|---|---|
| *A61K 38/04* | (2006.01) |
| *A61K 38/00* | (2006.01) |
| *A01N 37/18* | (2006.01) |
| *C07K 17/00* | (2006.01) |
| *C07K 5/00* | (2006.01) |
| *C07K 7/00* | (2006.01) |
| *C07K 16/00* | (2006.01) |

(52) U.S. Cl. ............................. 530/326; 514/2; 514/13; 514/14

(58) Field of Classification Search ....................... None
See application file for complete search history.

(56) References Cited

FOREIGN PATENT DOCUMENTS

| WO | WO/99/45954 | * | 9/1999 |
|---|---|---|---|
| WO | WO0142267 A1 | * | 6/2001 |
| WO | WO/01/90197 | * | 11/2001 |

OTHER PUBLICATIONS

Steve Pascolo et al., "A Mage-A1 HLA-A*0201 Epitope Identified by Mass Spectrometry," *Cancer Research*, 61:4072-4077 (2001).
Sacha Gnjatic et al., "Cross-Presentation of HLA Class I Epitopes from Exogenous NY-ESO-1 Polypeptides by Nonprofessional APCs," *The Journal of Immunology*, 170:1191-1196 (2003).

* cited by examiner

*Primary Examiner*—David J Blanchard
*Assistant Examiner*—Anne M. Gussow
(74) *Attorney, Agent, or Firm*—Fulbright & Jaworski LLP

(57) ABSTRACT

Peptides which consist of amino acid sequences found in MAGEA3 bind to HLA-Cw*07 molecules to form T cell epitopes. The therapeutic and diagnostic ramifications of this are the subject of this invention, as are various products obtained in the course of the development of the invention.

4 Claims, No Drawings

```
                        SEQUENCE LISTING

<160> NUMBER OF SEQ ID NOS: 36

<210> SEQ ID NO 1
<211> LENGTH: 16
<212> TYPE: PRT
<213> ORGANISM: Artificial Sequence
<220> FEATURE:
<223> OTHER INFORMATION: MAGEA3 derived sequence

<400> SEQUENCE: 1

Ala Ile Ile Ala Arg Glu Gly Asp Cys Ala Pro Glu Glu Lys Ile Trp
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: MAGEA3 derived sequence

<400> SEQUENCE: 2

Arg Glu Gly Asp Cys Ala Pro Glu Glu Lys Ile Trp Glu Glu Leu Ser
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Derived from Tyrosinase

<400> SEQUENCE: 3

Tyr Met Asp Gly Thr Met Ser Gln Val
1               5

<210> SEQ ID NO 4
<211> LENGTH: 9
<212> TYPE: PRT
<213> ORGANISM: Artificial Sequence
<220> FEATURE:
<223> OTHER INFORMATION: Derived from Tyrosinase

<400> SEQUENCE: 4

Met Leu Leu Ala Val Leu Tyr Cys Leu
1               5

<210> SEQ ID NO 5
<211> LENGTH: 10
<212> TYPE: PRT
<213> ORGANISM: Artificial Sequence
<220> FEATURE:
<223> OTHER INFORMATION: Derived from MelanA

<400> SEQUENCE: 5

Glu Leu Ala Gly Ile Gly Ile Leu Thr Val
1               5                   10

<210> SEQ ID NO 6
<211> LENGTH: 9
<212> TYPE: PRT
```

```
<213> ORGANISM: Artificial Sequence
<220> FEATURE:
<223> OTHER INFORMATION: Derived from MAGEA3

<400> SEQUENCE: 6

Ile Met Pro Lys Ala Gly Leu Leu Ile
1               5

<210> SEQ ID NO 7
<211> LENGTH: 9
<212> TYPE: PRT
<213> ORGANISM: Artificial Sequence
<220> FEATURE:
<223> OTHER INFORMATION: Derived from MAGEA3

<400> SEQUENCE: 7

Phe Leu Trp Gly Pro Arg Ala Leu Val
1               5

<210> SEQ ID NO 8
<211> LENGTH: 9
<212> TYPE: PRT
<213> ORGANISM: Artificial Sequence
<220> FEATURE:
<223> OTHER INFORMATION: Derived from MAGEA6

<400> SEQUENCE: 8

Val Arg Ile Gly His Leu Tyr Ile Leu
1               5

<210> SEQ ID NO 9
<211> LENGTH: 10
<212> TYPE: PRT
<213> ORGANISM: Artificial Sequence
<220> FEATURE:
<223> OTHER INFORMATION: Derived from MAGEA2

<400> SEQUENCE: 9

Tyr Leu Gln Leu Val Phe Gly Ile Glu Val
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Derived from MAGEA12

<400> SEQUENCE: 10

Phe Leu Trp Gly Pro Arg Ala Leu Val
1               5

<210> SEQ ID NO 11
<211> LENGTH: 10
<212> TYPE: PRT
<213> ORGANISM: Artificial Sequence
<220> FEATURE:
<223> OTHER INFORMATION: Derived from GnTV; Xaa may be Val or may be
      absent

<400> SEQUENCE: 11

Val Leu Pro Asp Val Phe Ile Arg Cys Xaa
                5                   10

<210> SEQ ID NO 12
<211> LENGTH: 9
<212> TYPE: PRT
```

```
<213> ORGANISM: Artificial Sequence
<220> FEATURE:
<223> OTHER INFORMATION: Derived from SSX2

<400> SEQUENCE: 12

Lys Ala Ser Pro Lys Ile Phe Tyr Val
1               5

<210> SEQ ID NO 13
<211> LENGTH: 9
<212> TYPE: PRT
<213> ORGANISM: Artificial Sequence
<220> FEATURE:
<223> OTHER INFORMATION: Derived from MAGEA10

<400> SEQUENCE: 13

Gly Leu Tyr Asp Gly Met Glu His Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Derived from MAGEA3

<400> SEQUENCE: 14

Glu Val Asp Pro Ile Gly His Leu Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: Derived from NY-ESO-1

<400> SEQUENCE: 15

Ser Leu Leu Met Trp Ile Thr Gln Cys
1               5

<210> SEQ ID NO 16
<211> LENGTH: 9
<212> TYPE: PRT
<213> ORGANISM: Artificial Sequence
<220> FEATURE:
<223> OTHER INFORMATION: Derived from MAGEA3

<400> SEQUENCE: 16

Ile Met Pro Lys Ala Gly Leu Leu Ile
1               5

<210> SEQ ID NO 17
<211> LENGTH: 9
<212> TYPE: PRT
<213> ORGANISM: Artificial Sequence
<220> FEATURE:
<223> OTHER INFORMATION: Derived from MAGEA3

<400> SEQUENCE: 17

Glu Val Asp Pro Ile Gly His Leu Tyr
1               5

<210> SEQ ID NO 18
<211> LENGTH: 10
<212> TYPE: PRT
<213> ORGANISM: Artificial Sequence
```

```
<220> FEATURE:
<223> OTHER INFORMATION: Derived from MAGEA4

<400> SEQUENCE: 18

Gly Val Tyr Asp Gly Arg Glu His Thr Val
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Derived from MAGEA1

<400> SEQUENCE: 19

Glu Ala Asp Pro Thr Gly His Ser Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: Derived from Tyrosinase

<400> SEQUENCE: 20

Ser Glu Ile Trp Arg Asp Ile Asp Phe
1               5

<210> SEQ ID NO 21
<211> LENGTH: 9
<212> TYPE: PRT
<213> ORGANISM: Artificial Sequence
<220> FEATURE:
<223> OTHER INFORMATION: Derived from Tyrosinase

<400> SEQUENCE: 21

Leu Pro Ser Ser Ala Asp Val Glu Phe
1               5

<210> SEQ ID NO 22
<211> LENGTH: 10
<212> TYPE: PRT
<213> ORGANISM: Artificial Sequence
<220> FEATURE:
<223> OTHER INFORMATION: Derived from MAGEA3

<400> SEQUENCE: 22

Met Glu Val Lys Pro Ile Gly His Leu Tyr
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Derived from GAGE-1,2,8

<400> SEQUENCE: 23

Tyr Arg Pro Arg Pro Arg Arg Tyr
1               5

<210> SEQ ID NO 24
<211> LENGTH: 9
<212> TYPE: PRT
<213> ORGANISM: Artificial Sequence
<220> FEATURE:
```

```
<223> OTHER INFORMATION: Derived from NY-ESO-1

<400> SEQUENCE: 24

Leu Ala Met Pro Phe Ala Thr Pro Met
1               5

<210> SEQ ID NO 25
<211> LENGTH: 9
<212> TYPE: PRT
<213> ORGANISM: Artificial Sequence
<220> FEATURE:
<223> OTHER INFORMATION: Derived from NY-ESO-1

<400> SEQUENCE: 25

Ala Arg Gly Pro Glu Ser Arg Leu Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Derived from GAGE-3,4,5,6,7

<400> SEQUENCE: 26

Tyr Tyr Trp Pro Arg Pro Arg Arg Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: Derived from BAGE-1

<400> SEQUENCE: 27

Ala Ala Arg Ala Val Phe Leu Ala Leu
1               5

<210> SEQ ID NO 28
<211> LENGTH: 12
<212> TYPE: PRT
<213> ORGANISM: Artificial Sequence
<220> FEATURE:
<223> OTHER INFORMATION: Derived from MAGEA3

<400> SEQUENCE: 28

Thr Gln His Phe Val Gln Glu Asn Tyr Leu Glu Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Derived from NY-ESO-1

<400> SEQUENCE: 29

Ser Leu Leu Met Trp Ile Thr Gln Cys Phe Leu
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Derived from MAGEA3
```

```
<400> SEQUENCE: 30

Ala Glu Leu Val His Phe Leu Leu Leu Lys Tyr Arg Ala Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Derived from MAGEA3, A6, A2

<400> SEQUENCE: 31

Leu Leu Lys Tyr Arg Ala Arg Glu Pro Val Thr Lys Ala Glu
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Derived from MAGEA-12

<400> SEQUENCE: 32

Ala Glu Leu Val His Phe Leu Leu Leu Lys Tyr Arg Ala Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Derived from MAGE-A1

<400> SEQUENCE: 33

Glu Tyr Val Ile Lys Val Ser Ala Arg Val Arg Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Derived from MAGE-A1

<400> SEQUENCE: 34

Leu Leu Lys Tyr Arg Ala Arg Glu Pro Val Thr Lys Ala Glu
                5                   10

<210> SEQ ID NO 35
<211> LENGTH: 20
<212> TYPE: PRT
<213> ORGANISM: Artificial Sequence
<220> FEATURE:
<223> OTHER INFORMATION: Derived from NY-ESO-1

<400> SEQUENCE: 35

Pro Gly Val Leu Leu Lys Glu Phe Thr Val Ser Gly Asn Ile Leu Thr
1               5                   10                  15

Ile Arg Leu Thr
            20

<210> SEQ ID NO 36
<211> LENGTH: 18
<212> TYPE: PRT
<213> ORGANISM: Artificial Sequence
```

-continued

```
<220> FEATURE:
<223> OTHER INFORMATION: Derived from NY-ESO-1

<400> SEQUENCE: 36

Ala Ala Asp His Arg Gln Leu Gln Leu Ser Ile Ser Ser Cys Leu Gln
1               5                   10                  15

Gln Leu
```

ISOLATED PEPTIDE WHICH BINDS TO HLA-CW*07 AND USES THEREOF

RELATED APPLICATIONS

This application claims priority benefit under Title 35, U.S.C. § 119(e) of provisional application No. 60/504,874, filed Sep. 22, 2003, which is incorporated by reference in its entirety.

FIELD OF THE INVENTION

This invention relates to peptides which form immunologically active complexes with MHC molecules. More particularly, it involves peptides based upon amino acid sequences found in the molecule referred to as "MAGEA3," which form complexes with the MHC molecule HLA-Cw*07.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T cells in the recipient animal, and provoke a cytolytic T cell response with lysis of the transplanted cells. This evidence was first obtained with tumors induced in vitro by chemical carcinogens, such as methylcholanthrene. The antigens expressed by the tumors and which elicited the T cell response were found to be different for each tumor. See Prehn, et al., *J. Natl. Canc. Inst.*, 18: 769-778 (1957); Klein, et al., *Cancer Res.*, 20:1561-1572 (1960); Gross, *Cancer Res.*, 3:326-333 (1943), Basombrio, *Cancer Res.*, 30:2458-2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, *J. Natl. Canc. Inst.*, 53:333-1336 (1974).

While T cell mediated immune responses were observed for the types of tumor described supra, spontaneous tumors were thought to be generally non-immunogenic. These were therefore believed not to present antigens which provoked a response to the tumor carrying subject. See Hewitt, et al., *Brit. J. Cancer*, 33:241-259 (1976).

The family of tum⁻ antigen presenting cell lines are immunogenic variants obtained by mutagenesis of mouse tumor cells or cell lines, as described by Boon, et al., *J. Exp. Med.*, 152:1184-1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See, Boon, et al., *Proc. Natl. Acad. Sci USA*, 74:272 (1977), the disclosure of which is incorporated by reference. Many tumor types have been shown to exhibit this phenomenon. See, e.g., Frost, et al., *Cancer Res.*, 43:125 (1983).

It appears that tum⁻ variants fail to form progressive tumors because they elicit an immune rejection process. The evidence in favor of this hypothesis includes the ability of "tum⁻" variants of tumors, i.e., those which do not normally form tumors, to do so in mice with immune systems suppressed by sublethal irradiation, Van Pel, et al. *Proc. Natl, Acad. Sci. USA,* 76:5282-5285 (1979); and the observation that intraperitoneally injected tum⁻ cells of mastocytoma P815 multiply exponentially for 12-15 days, and then are eliminated in only a few days in the midst of an influx of lymphocytes and macrophages (Uyttenhove, et al., *J. Exp. Med.*, 152:1175-1183 (1980)). Further evidence includes the observation that mice acquire an immune memory which permits them to resist subsequent challenge to the same tum⁻ variant, even when immunosuppressive amounts of radiation are administered with the following challenge to the same tum⁻ variant, even when immunosuppressive amounts of radiation are administered with the following challenge of cells (Boon, et al., *Proc. Natl, Acad. Sci. USA*, 74:272-275 (1977); Van Pel, et al., supra; Uyttenhove, et al., supra). Later research found that when spontaneous tumors were subjected to mutagenesis, immunogenic variants were produced which did generate a response. Indeed, these variants were able to elicit an immune protective response against the original tumor. See Van Pel, et al., *J. Exp. Med.*, 157:1992-2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon, et al., *Cancer Res.*, 48:2975-1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro, i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., *Adv. Cancer Res.*, 24:1-59 (1977); Boon, et al., *J. Exp. Med.*, 152:1184-1193 (1980); Brunner, et al., *J. Immunol.*, 124:1627-1634 (1980); Maryanski, et al., *Eur. J. Immunol.*, 124:1627-1634 (1980); Maryanski, et al., *Eur. J. Immunol.*, 12:406-412 (1982); Palladino, et al., *Canc. Res.*, 47:5074-5079 (1987). This type of analysis is required for other types of antigens recognized by CTLs, including minor histocompatibility antigens, the male specific H-Y antigens, and a class of antigens, referred to as "tum⁻" antigens, and discussed herein.

A tumor exemplary of the subject matter described supra is known as P815. See DePlaen, et al., *Proc. Natl. Acad. Sci. USA*, 85:2274-2278 (1988); Sikora, et al., *EMBO J.*, 9:1041-1050 (1990), and Sibille, et al., *J. Exp. Med.*, 172:35-45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra) and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Siblle, supra, and Lurquin, et al., *Cell,* 58:293-303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

U.S. Pat. No. 5,342,774, the disclosure of which is incorporated by reference, disclosed three members of a family of the genes referred to hereafter as the "MAGE" family of genes. MAGEA1, A2 and A3 are disclosed therein. Also see Traversari, et al., *J. Exp. Med.,* 176:1453-1457 (1993); van der Bruggen, et al., *Science,* 254:1643-147 (1991), the disclosures of which are incorporated by reference. Additional members of the MAGE family have been discovered and are disclosed in, e.g., DePlaen, et al., *Immunogenetics,* 40:360 (1994), and U.S. Pat. No. 5,612,201 to DePlaen, both of which are incorporated by reference. With respect to MAGEA1, in addition to the '774 patent, see e.g. U.S. Pat. No. 5,925,729.

The genes are useful as a source for the isolated and purified tumor rejection antigen precursor and the TRA themselves, either of which can be used as an agent for treating the cancer for which the antigen is a "marker", as well as in various diagnostic and surveillance approaches to oncology, discussed infra. It is known, for example that tum⁻ cells can be used to generate CTLs which lyse cells presenting different tum⁻ antigens as well as tum⁺ cells. See, e.g., Maryanski, et al., *Eur. J. Immunol.,* 12:401 (1982); and Van den Eynde, et al., Modem Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini, et al., *Immuno. Today,* 8:385-389 (1987)). This response has been particularly well studied for melanomas, and MLTC have been carried out either with peripheral blood cells or with tumor infiltrating lymphocytes. Examples of the literature in this area including Knuth, et al., *Proc. Natl. Acad. Sci. USA,* 86:2804-2802 (1984); Mukherji, et al., *J. Exp. Med.,* 158:240 (1983); Hérin, et al., *Int. J. Canc.,* 39:390-396 (1987); Topalian, et al., *J. Clin. Oncol.,* 6:839-853 (1988). Stable cytotoxic T cell clones ("CTLs" hereafter) have been derived from MLTC responder cells, and these clones are specific for the tumor cells. See Mukherji, et al., supra, Hérin, et al., supra, Knuth, et al., supra. The antigens recognized on tumor cells by these autologous CTLs do not represent a cultural artifact, since they are found on fresh tumor cells. Topalian, et al., supra; Degiovanni, et al., *Eur. J. Immul.,* 20:1865-1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra.

Additional work has focused upon the presentation of TRAs by the class of molecules known as human leukocyte antigens, or "HLAs". This work has resulted in several unexpected discoveries regarding the field. Specifically, in U.S. Pat. No. 5,405,940, the disclosure of which is incorporated by reference, nonapeptides including a MAGEA3 derived peptide, are taught which are presented by HLA-A1 molecules. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

Additional peptides have been identified which consist of amino acid sequences found in MAGE-3, but which bind to different MHC molecules. See, e.g., U.S. Pat. Nos. 5,554,506, 5,585,461, 5,591,430 and 6,091,987 which describe peptides which bind to HLA-A2 molecules, and also see U.S. Pat. Nos. 5,965,535, 6,291,430 and 6,369,211, which teach peptides consisting of amino acid sequences found in MAGE-3, which bind to MHC Class II molecules. See, e.g., Tanzarella, et al., *Canc. Res.,* 59:2668-74 (1999), teaching a MAGEA3 based peptide which binds to HLA-B37, as well as Kawashima, et al., *Hum Immunol.,* 59:1-14 (1998); Tanako, et al., *Cancer Res.,* 57:4465-68 (1997); Oiso, et al., *Int. J. Cancer,* 81:387-94 (1999), and Herman, et al., *Immunogenetics,* 43:377-83 (1996), which collectively teach MAGEA3 based peptides which bind to HLA-A*0201, A24, B*4402 and B*4403. These papers are all incorporated by reference in their entirety.

It is important to note that different approaches have been taken to identifying the peptides described herein with different ramifications. For example, Gaugler et al., *J. Exp. Med.* 179:921-930 (1994) and Tanzarella, et al., supra, secured CTLs from melanoma patients following autologous, mixed lymphocyte tumor cell cultures. With respect to the other references cited herein, "motif analysis", using information found in, e.g., Ramensee, et al., *Immunogenetics,* 41:178-228 (1995), incorporated by reference, was applied to the complete sequence of MAGEA3 protein to identify potential HLA molecule binders. These were then tested, and active molecules identified thereby.

This approach, i.e., employing motif analysis, has been found to exhibit a major drawback in that several peptide specific CTL generated using the synthetic peptides, do not recognize HLA matched tumor cells which express MAGE-3 endogenously. There have been two explanations proposed for this. One is that the peptides at issue are not generated efficiently by the natural processing and presentation machinery of the cells. The second is that the CTLs obtained using high concentrations of the synthetic peptides have low affinity for the target. See Dahl, et al., *J. Immunol.,* 157:239-246 (1996).

MAGEA3 is expressed in about 75% of metastatic melanomas, and in 35-50% of esophageal, head and neck, lung. and bladder carcinomas. See, e.g., Gaugler, et al., supra. Boon, et al., Cancer Vaccines: Cancer Antigens, Shared Tumor Specific Antigens" in Rosenberg, ed., *Principles and Practice of The Biologic Therapy of Cancer* (Philadelphia, JB Lippincott Williams & Wilkins, 2000), pp. 493-504. Hence, there is interest in having additional methodologies available for identifying peptides consisting of sequences found in MAGEA3, especially those which form complexes with MHC molecules other than those set forth, supra.

A new strategy has been developed for identifying only naturally or well processed tumor antigens. Dendritic cells transduced with gene MAGEA3 are used as stimulator cells for autologous $CD8^+$ T cells. See, e.g., Luiten, et al., *Tissue Antigens,* 55:149-152 (2000); Chaux, et al., *J. Immunol.,* 163: 2928-36 (1999); Luiten, et al., *Tissue Antigens,* 56:77-81 (2000); Schultz, et al., *Tissue Antigens,* 57:103-9 (2001), and Van den Eynde: Cancer Immunity 2001: www.cancerimmunity.org/peptidedatabase/tcellepitopes.htm., all of which are incorporated by reference, for examples of the application of this technique, with identification of relevant antigenic peptides.

DETAILED DESCRIPTION OF PREFERRED EMBODIMENTS

EXAMPLE 1

This example describes the generation of dendritic cells ("DCs" hereafter), from peripheral blood mononucleic cells (PBMCs).

PBMCs were isolated from a standard, buffy coat preparation of a cancer free individual, using standard methods. The $CD14^+$ portion of this population were separated therefrom, using magnetic beads, in accordance with the manufacturer's instructions. The monocytes were then permitted to differentiate into immature DCs, by culturing in X-VIVO 15™ medium that had been supplemented with 1%, heat inactivated human AB serum, with recombinant GM-CSF and IL-4 at 1000 U/ml and 100 U/ml, respectively, to a cell density of $1\times10^6$ DC/ml. The cells were then incubated in a humidified atmosphere with 5% $CO_2$ at 37° C. After three days, the cells were transduced, as discussed infra.

EXAMPLE 2

After three days, the cells described supra were immature DCs, at an early stage of culture. These cells were transduced with HIV-1 derived, triple helix containing, self-inactivating lentiviral particles, which encoded the fusion protein huIi80MAGEA3, as described herein.

The multiple attenuated packaging plasmid pCMVΔR8.9, and VSV.G encoding plasmid pMD.G were used, as was transfer vector pHR trip CMVhuIi80MAGEA3-Ires-tNGFr SIN, which is described by Breckpot, et al., *J. Gene Med.,* 5(8):657-667 (2003). The vector encodes the first 80 amino acids of the human invariant chain, fused to the entire MAGEA3 coding sequence.

VSV.G pseudotyped, HIV-1 derived viral particles were generated, by cotransfection of the transfer vector, the VSV.G expressing construct pMD.G, and the packaging construct pCMVΔR8.9, into 293T cells.

Lentivirus containing supernatant was collected, 48 and 72 hours after transfection, filtered through a 0.22:m, pore-sized filter, and concentrated, 200×, via ultracentrifugation, for 140 minutes, at 19500 rpm. Viral stock was stored at −80° C., in X-VIVO 15™ medium supplemented with 1% human AB serum.

Viral titres were then determined by infecting 293 T cells with serial dilutions of the stock. The number of tNGFR positive cells was scored, 72 hours after infection, to determine titer. Titer was calculated as:

$$\frac{[(\%\ TngFR\ \text{positive cells}) \times (\text{number of cells transduced}) \times \text{dilution factor}]}{(100 \times (\text{transduction volume}))}$$

The DCs, described supra, were then transfected with the viral vectors, by resuspending $1.0\times10^6$ of the DCs of example 1, in 1 ml X-VIVO 15™, supplemented with 1% human AB serum, 10 :g/ml protamine sulphate, 100 U/ml IL-4, and 1000 U/ml GM-CSF, and adding recombinant lentiviruses encoding MAGEA3 at an MOI of 15. Immature, transduced DCs were then cultured, at a density of $1\times10^6$ cells/ml, for an additional 3 days.

At this point, the cells were allowed to mature to cell densities of $5\times10^5$ DC/ml, in the X-VIVO 15™ medium, with 1% human AB serum, together with 100 U/ml IL-∃, 1000 U/ml IL-6, 100 U/ml TNF∀, and 1 :g/ml PGE2. See Jonuleit, et al., *Eur. J. Immunol.,* 27(12):3135-3142 (1997). This cocktail of inflammatory cytokines induces maturation of the DCs, which were then used in the experiments which follow. Prior to their use, the DCs were cryopreserved in 1 ml 20% albumin solution, with 10% DMSO, and $1-5\times10^6$ cells/vial. Cells were frozen to −80° C., using standard methods. When needed, they were thawed in a 37° C. waterbath, until small ice crystals were seen, and then cold Hank's Balanced Salt Solution was added, dropwise. DCs were then pelleted in a pre-cooled centrifuge, and resuspended in 5 ml/$5\times10^6$ cells of pre-warmed X-VIVO 15™ medium with 1% human AB serum. Cells were counted after 15 minutes.

EXAMPLE 3

The phenotype of these DCs was analyzed via flow cytometry. Cells were stained by mixing them for 30 minutes on ice in a medium of PBS with 1% BSA and 0.02% sodium azide, with FITC or phycoerythrin conjugated monoclonal antibodies specific for CD80, CD83, and CD86. Further, anti-hutNGFR and anti-HLA-DR antibodies were biotinylated, and contacted with conjugates of streptavidin and phycoerythrin.

FACS showed a phenotype of $HLA-DR^{+++}$, $CD80^+$, $CD83^+$, $CD86^{++}$, indicating a mature phenotype.

Following isolation of $CD14^+$ cells, in accordance with example 1, autologous $CD8^+$ responder T cells were isolated in the same way.

Mature, lentivirally transduced day 7 DCs were harvested, washed in X-VIVO 15™, and then mixed with autologous $CD8^+$ cells, in round bottom, 96 well plates, at a T cell DC ratio of 10/1 ($10^5/10^4$) in 200:1 of X-VIVO 15™, supplemented with 1% human AB serum, with 1000 U/ml IL-6, and 10 ng/ml IL-12. On both day 7 and day 14 of the experiment, additional lentivirus transduced cells were thawed, and used to restimulate the $CD8^+$ cells, in medium to which 10 U/ml IL-2, and 5 ng/ml IL-7 were added.

One week after the last stimulation, an aliquot of each T cell microculture $\pm 5\times10^3$ T cells, was mixed with $2\times10^4$ autologous, EBV transfected B cells, which had been transduced to express huIi-80MAGEA3. The procedures of Chaux, et al., *J. Exp. Med.,* 189:767-778 (1994) and Schultz, et al., *Cancer Res.,* 60:6272-6275 (2000), both of which are incorporated by reference, were used. As a control, non-transduced autologous EBV-B cells were used.

Release of IFN-γ was measured, by co-culturing $5\times10^{3+}$ of the $CD8^+$ T cells with $2\times10^4$ of the EBV-B cells, in a round bottom, 96 well plate, in 200 μl of IMEM, with 10% AB serum. In addition, L-asparagene, L-arginine, and L-glutamine were added, together with 25 U/ml of IL-2. After 24 hours, supernatant was collected, and IFN-γ content measured via a standard ELISA.

Four microcultures produced significant amounts of IFN-γ, and were used in the experiments which follow.

EXAMPLE 4

The four microcultures referred to supra, were cloned via limiting dilution. Irradiated, allogenic PBMCs ($5\times10^3$ cells/well), were combined, with $5\times10^3$ LG2 EBV B cells as feeder cells, per well, in a round bottom, 96 well plate. Irradiated, autologous, retrovirally transduced EBV B cells, as described supra, were added, ($5\times10^3$ cells/well), as stimulator cells. In addition, 50 U/ml of IL-2, 5 U/ml IL-4, and 5 ng/ml IL-7 were added, together with 0.1 μg/ml of phytohemagglutinin (PHA).

This culturing resulted in establishment of CD8+ T cell clone "MD1." It was grown in complete IMEM, supplemented with the cytokines and PHA, as discussed supra, and passaged with feeder and stimulator cells ($1\times10^6$ LG2 EBV B and $2\times10^5$ autologous, retrovirally transduced EBV B cells/well) in a 24 well plate, every 7-10 days.

EXAMPLE 5

The ability of CD8+ T cell clone MD1 to lyse MAGEA3 expressing cells was tested, in a standard $^{51}$Cr release assay. Target EBV-B cells, were labeled with 100 μCi of Na($^{51}$Cr)O$_4$ for one hour, and then washed extensively. The targets were autologous, non-transduced EBV-B cells, K562 cells, and EBV-B cells transduced with MAGEA3 encoding vector, as described, supra. Effector: target ratios of 10/1 5/1, and 1/1 were used. Triplicate cultures were run.

The data indicated that the T cell clone, MD1, lysed the autologous, MAGEA3 expressing EBV-B cells, but not the others.

In view of this, experiments were then carried out to determine the epitope recognized.

EXAMPLE 6

In these experiments, peptides based upon MAGEA3, sixteen amino acids in length, were synthesized, using standard methods. These peptides overlapped by 12 amino acids, and covered the entire MAGEA3 amino acid sequence.

Autologous EBV-B cells were then pulsed with 10 μg/ml of peptide, at a density of $2\times10^6$ cells/ml, in serum free medium, for 2 hours at 37° C. The peptide loaded cells were used in IFN-γ assays, as described, supra.

Two overlapping peptides consisting of amino acids 207-222 and 211-226 of MAGEA3 were found to provoke secretion of 681 pg/ml, and 1200 pg/ml of IFN-γ, respectively by the MAGEA3 specific T cells.

```
AIIAREGDCAPEEKIW      (SEQ ID NO: 1)

REGDCAPEEKIWEELS      (SEQ ID NO: 2)
```

EXAMPLE 7

The donor of the cells used in the experiments described herein had been typed as HLA-A*02/03, B*07, Cw*07. In order to determine which of these molecules was the presenting HLA molecule, EBV-B cells were chosen which expressed one or two, but not all three of these HLA molecules, were loaded with 10 μg/ml of SEQ ID NO: 2, and tested in IFN-γ assays, as discussed supra.

The results indicated that HLA-Cw*0701 was the presenting molecule, since only peptide pulsed EBV-B cells expressing HLA-Cw*0701 were able to stimulate T cell IFN-γ release.

EXAMPLE 8

The activity of clone MD1 was tested in this example.

Retroviral vectors MAGEA3 cDNA, as well as processes for transducing EBV B cells were known. See Chaux, et al., *J. Exp. Med.*, 189:767-778 (1999), and Schultz, et al., *Cancer Res.*, 60:6272-6275 (2000), both of which are incorporated by reference. The procedures described in these references were used, together with vector pMFG which encodes MAGEA3, were used to transduce human embryonic kidney cell line 293T.

Retrovirally transfected 293T cells or untrasfected cancer cells were co-transfected ($1\times10^6$ cells/well) using the standard calcium phosphate method, with either 5 μg of HLA-Cw*0701, or HLA-A*0101, and 5 μg of a plasmid encoding β-microglobulin. The cells were incubated for 24 hours, at 37° C. and 5% $CO_2$. The transfectants were then prepared as targets for a standard $^{51}$Cr release assay, as described supra. An effector target ratio of 1:1 was used.

Only cells cotransfected with MAGEA3 and HLA-Cw*0701 were lysed by the MAGEA3 specific MD1 T cell line described supra.

EXAMPLE 9

As noted, supra, both SEQ ID NOS: 1 and 2 led to lysis by MAGEA3 specific T cell clone IE9-4A7. These peptides are too long for MHC-Class I presentation. As such, overlap of the peptides was studied, and peptides were synthesized as a result. These peptides were:

```
REGDCAPEEKIWEEL;  (amino acids 1-15 of SEQ ID NO: 2)

APEEKIWEEL;       (amino acids 6-15 of SEQ ID NO: 2)

REGDCAPEEKIW;     (amino acids 1-12 of SEQ ID NO: 2)

REGDCAPEEKI,      (amino acids 1-11 of SEQ ID NO: 2)
and

GDCAPEEKI.        (amino acids 3-11 of SEQ ID NO: 2)
```

Each peptide was tested in the $^{51}$Cr release assay used to test SEQ ID NOS: 1 and 2. Only the peptides consisting of amino acids 1-11 of SEQ ID NO: 2 was recognized and provoked T cell lysis.

As a follow up to these experiments, further work was done to determine the N- and C-terminus of the minimum peptide necessary for lysis.

The following peptides were synthesized:

```
(A) DCAPEEK;     (amino acids 3-10 of SEQ ID NO: 2)

(B) CAPEEKI;     (amino acids 4-11 of SEQ ID NO: 2)

(C) EGDCAPEE;    (amino acids 2-9 of SEQ ID NO: 2)

(D) EGDCAPEEK;   (amino acids 2-10 of SEQ ID NO: 2)

(E) EGDCAPEEKI.  (amino acids 2-11 of SEQ ID NO: 2)
```

These were tested in $^{51}$Cr release assays, as described, supra with SEQ ID NO: 2, and a peptide consisting of amino acids 1-12 of SEQ ID NO: 2 as controls.

Autologous EBV B cells were loaded with varying concentrations of peptide (10 µM to 1 nM, 3× dilutions). The peptide of SEQ ID NO: 2, amino acids 1-12 of SEQ ID NO: 2, (D), and (E) led to lysis, whereas the 8 mers did not. At an effector/target ratio of 5:1, about 34% of autologous EBV-B cells loaded with D, at a concentration of 1 nM, were lysed.

EXAMPLE 10

The minimal peptide EGDCAPEEK, is also found within the amino acid sequences of MAGEA2, A6, and A12. As such experiments were carried out to determine if the CTL clone discussed herein lysed cells which expressed these genes.

Target cells for the assay were 293T cells, which had been transiently transfected using 4 µg of plasmids encoding MAGE-A2, A6, A12, tyrosinase, or MAGEA3.

Cotransfection of target cells with HLA-Cw*07 and β2 microglobulin was also carried out. The same $^{51}$Cr lysis assay was carried out, as described supra.

All cells which were transfected with MAGEA2, A3, A6, or A12, and HLA-Cw*0701/B$_2$m were lysed, while those which were transfected with HLA-A*0101 or tyrosinase were not lysed.

EXAMPLE 11

In further experiments, the ability of the CTL to recognize the peptide when naturally presented by tumor cells was tested.

Four tumor cell lines, i.e., LB10171-HNSC, LB20-MEL, LB1077-MEL, and CP50-MEL, which express both HLA-Cw*07 and MAGEA3 were tested, in the IFN-γ release assay described supra.

Significant amounts of IFN-γ, ranging from 400-700 pg/ml were produced by co-culture with the tumor cells.

When the tumor lines were loaded with 10 µg/ml of the minimal peptide, comparable IFN-γ amounts ranging from 600-1200 pg/ml, were produced following co-culture with the T cells.

EXAMPLE 12

Tumor lines which express MAGEA2/A6 and HLA-Cw*07 but not MAGEA3, were tested in the same assay.

Those cells which expressed HLA-Cw*07 and one of MAGEA2 or A6 were lysed efficiently, at an effector:target ratio of 10:1.

The foregoing disclosure sets forth various features of the invention. These include isolated peptides which are processed to peptides that form immunogenic complexes with HLA-Cw*07 molecules. The peptides of the invention comprise amino acids 6-14 of SEQ IDNO: 1, i.e.:

AIIAREGDCAPEEKIW concatenated to from 1 to 30 additional amino acids at the N and/or C terminus, preferably from 5-10 additional amino acids, most preferably from 1-6 amino acids, such as the peptide of SEQ ID NO: 1, supra or SEQ ID NO: 2, i.e.,

REGDCAPEEKIWEELS

Preferably, the concatenated amino acids are identical to the amino acid sequence which precedes E or follows K in the full length amino acid sequence of MAGEA2, A3, A6 or A12, but the concatenated amino acids also accommodate variations, such as conservative substitutions, deletions, additions and so forth. The peptides of the invention possess the functional properties of being taken up by antigen presenting cells, such as dendritic cells, and being processed to the 9 amino acid sequence described supra. For example, the experiments supra show efficacy with peptides, such as amino acids 1-11 of SEQ ID NO: 2, amino acids 2-10 of SEQ ID NO: 2, and/or amino acids 2-11 of SEQ ID NO: 2. See, Gnjatic, et al., *J. Immunol.*, 170:1191-1196 (2003) incorporated by reference.

Preferably, the antigen presented cells which take up the peptides are cells which present HLA-Cw*07 molecules on their surface.

Also a feature of this invention are isolated cytolytic T cells which are specific for complexes of HLA-Cw*07 molecules and the 9 amino acid sequence referred to supra, which do not recognize other complexes, including complexes of the sequence and different HLA molecules. As was shown, supra, such cytolytic T cells can be prepared using standard methodologies, including those described herein.

In connection with the cytolytic T cell lines of the invention, various methods can be used to identify and to secure these. Such methodologies include, i.e., FACS or other analytical methods, preferably in combination with molecules, such as tetrameric compounds of avidin or streptavidin, biotin, and HLA/peptide complexes, to identify relevant CTLs from samples.

The ability of the peptides to form recognizable complexes makes them useful as therapeutic agents in conditions such as cancer, including melanoma, lung, breast, head and neck, and other cancer types, such as those described in, e.g., Principals and Practic of The Biologic Therapy of Cancer (Lippincott Williams and Wilkens, 3$^{rd}$ ed., 2000), p. 499, incorporated by reference, where the peptide forms a complex with the HLA molecule, leading to recognition by a CTL, and lysis thereby. As was shown, supra, CTLs which recognize the complexes occur naturally in patients, so administration of the peptide of the invention to an HLA-Cw*07 positive subject in need of a cytolytic T cell in response is another feature of the invention. Such subjects may be, e.g., cancer patients, such as melanoma patients. Such patients may receive the peptide of the invention, or "cocktails" which comprise more than one HLA binding peptide, as long as the peptide cocktail includes the peptide of the invention. The peptide component of such cocktails may consist of the peptides described herein, or may combine some peptides disclosed herein with other peptides known in the art, such as the following, which bind to Class I or Class II MHC.

| PEPTIDE SEQUENCE | ANTIGEN | HLA | SEQ ID NO: |
|---|---|---|---|
| YMDGTMSQV | TYROSINASE | A2 | 3 |
| MLLAVLYCL | TYROSINASE | A2 | 4 |
| ELAGIGILTV | MELAN-A | A2 | 5 |

-continued

| PEPTIDE SEQUENCE | ANTIGEN | HLA | SEQ ID NO: |
|---|---|---|---|
| IMPKAGLLI | MAGEA3 | A2 | 6 |
| FLWGPRALV | MAGEA3 | A2 | 7 |
| VRIGHLYIL | MAGEA6 | Cw7 | 8 |
| YLQLVFGIEV | MAGEA2 | A2 | 9 |
| FLWGPRALV | MAGEA12 | A2 | 10 |
| VLPDVFIRC(V) | GnTV | A2 | 11 |
| KASPKIFYV | SSX2 | A2 | 12 |
| GLYDGMEHL | MAGEA10 | A2 | 13 |
| EVDPIGHLY | MAGEA3 | A1 | 14 |
| SLLMWITQC | NY-ESO-1 | A2 | 15 |
| IMPKAGLLI | MAGEA3 | A24 | 16 |
| EVDPIGHLY | MAGEA3 | B35 | 17 |
| GVYDGREHTV | MAGEA4 | A2 | 18 |
| EADPTGHSY | MAGEA1 | A1, B35 | 19 |
| SEIWRDIDF | TYROSINASE | B44 | 20 |
| LPSSADVEF | TYROSINASE | B35 | 21 |
| MEVKPIGHLY | MAGEA3 | B18, B44 | 22 |
| YRPRPRRY | GAGE-1,2,8 | Cw6 | 23 |
| LAMPFATPM | NY-ESO-1 | Cw3 | 24 |
| ARGPESRLL | NY-ESO-1 | Cw6 | 25 |
| YYWPRPRRY | GAGE-3,4,5,6,7 | A29 | 26 |
| AARAVFLAL | BAGE-1 | Cw16 | 27 |
| TQHFVQENYLEY | MAGEA3 | DP4 | 28 |
| SLLMWITQCFL | NY-ESO-1 | DP4 | 29 |
| AELVHFLLLKYRAR | MAGEA3 | DR13 | 30 |
| LLKYRAREPVTKAE | MAGEA3,A6,A2 | DR13 | 31 |
| AELVHFLLLKYRAR | MAGE-A-12 | DR13 | 32 |
| EYVIKVSARVRF | MAGE-A1 | DR15 | 33 |
| LLKYRAREPVTKAE | MAGE-A1 | DR13 | 34 |
| PGVLLKEFTVSGNILTIRLT | NY-ESO-1 | DR4 | 35 |
| AADHRQLQLSISSCLQQL | NY-ESO-1 | DR4 | 36 |

In an especially preferred embodiment, one administers a cocktail of peptides based upon the HLA profile of the subject being treated. Based upon known Class I peptide binding motifs, such as those set forth by Rammensee, et al., supra, peptides such as those set forth at SEQ ID NOS: 5-38 would be expected to bind to other HLA-Class I or II alleles, such as HLA-A1; A3, B7, B8, B15, B27, B44, B51, DP4, DR4 in addition to HLA-A2, and subtypes thereof. Further, if appropriate, one or more peptides which bind to HLA-A2, HLA-B7, HLA-Cw6 and so forth, can be admixed, preferably in the presence of an adjuvant like GM-CSF, Montanide, alum, or another adjuvants well known to the art, such as CpG. See U.S. Pat. Nos. 6,339,068; 6,239,116; 6,207,646 and 6,194,388, all of which are incorporated by reference. Also possible as therapeutic agents are peptide pulsed, autologous dendritic cells. See, e.g., Jonuleit, et al., Int. J. Cancer, 93(2):243-51 (2001); Schuler-Thurner, et al., J. Immunol., 165(6):3492-6 (2000); Thurner, et al., J. Exp. Med., 190(11):1669-78 (1999), all of which are incorporated by reference and show, e.g., the use of peptide pulsed dendritic cells as vaccines and as adjuvants. Such combinations of peptides, in the form of compositions, are another feature of the invention, either alone or in combination with such adjuvants. Similarly, one can administer cytolytic T cells specific for the peptide/HLA-Cw*07 complexes, such as autologous CTLs, which can be prepared as described in the preceding examples. These CTLs, which are specific for complexes amino acids 6-14 of SEQ ID NO: 1 and HLA-Cw*07, and no other complexes, are a further feature of the invention.

Yet a further feature of the invention are nucleic acid molecules which consist of nucleotide sequences that encode the peptide of the invention. Such nucleic acid molecules may be used to encode the peptides of the invention, and may be combined into expression vectors, operably lined to a promoter. More than one sequence can be combined in such expression vectors, as can nucleic acid molecules which encode HLA-Cw*07 molecules. The constructs can be used to transfect cells, so as to generate the CTLs, or for administration to subjects in need of a cytolytic T cell response or augmenting of a pre-existing T cell response. Such administration could be one of, e.g., administering vector constructs as described, heterologous expression vectors, peptides or recombinant proteins, such as the full length proteins, preferably in recombinant form, from which one or more of the peptides are derived as discussed supra.

The invention also relates to the use of the peptides, CTLs, and other, immunologically active components, such as antibodies and T cell receptors, to diagnose pathological conditions such as cancer, melanoma in particular. As was shown, supra, MAGEA2, A3, A6 and A12 are expressed in cancer cells and the presence of complexes of the amino acids 6-14 of SEQ ID NO: 1 and HLA-Cw*07 is indicative of a pathological condition. By determining the interaction of the immunologically active component and the complex (by way of, e.g., antibody binding, TNF release, cell lysis, etc.), one can diagnose the pathology, or even determine the status of the pathology via comparing a value to a pre-existing value for the same parameter.

Also a part of this invention are antibodies, e.g., polyclonal and monoclonal, and antibody fragments, e.g., single chain Fv, Fab, diabodies, etc., that specifically bind the peptides or HLA/peptide complexes disclosed herein. Preferably, the antibodies, the antibody fragments and T cell receptors bind the HLA/peptide complexes in a peptide-specific manner. Such antibodies are useful, for example, in identifying cells presenting the HLA/peptide complexes. Such antibodies are also useful in promoting the regression or inhibiting the progression of a tumor which expresses complexes of the HLA and peptide. Polyclonal antisera and monoclonal antibodies specific to the peptides or HLA/peptide complexes of this invention may be generated according to standard procedures. See e.g., Catty, D., Antibodies, A Practical Approach, Vol. 1, IRL Press, Washington D.C. (1988); Klein, J. Immunology: The Science of Cell-Non-Cell Discrimination, John Wiley and Sons, New York (1982); Kennett, R., et al., Monoclonal Antibodies, Hybridoma, A New Dimension In Biological Analyses, Plenum Press, New York (1980); Campbell, A., Monoclonal Antibody Technology, in Laboratory Techniques and Biochemistry and Molecular Biology, Vol. 13 (Burdon, R. et al. EDS.), Elsevier Amsterdam (1984); Eisen, H. N., Microbiology, third edition, Davis, B. D. et al. EDS. (Harper & Rowe, Philadelphia (1980); Kohler and Milstein, *Nature*, 256:495 (1975) all incorporated herein by reference.) Methods for identifying Fab molecules endowed with the antigen-specific, HLA-restricted specificity of T cells has been described by Denkberg et al., *PNAS*, 99:9421-9426 (2002) and Cohen et al., *Cancer Research*, 62:5835-5844 (2002) both incorporated herein by reference). Methods for generating and identifying other antibody molecules, e.g., scFv and diabodies are well known in the art, see e.g., Bird et al., *Science*, 242:423-426 (1988); Huston et al., *Proc. Natl. Acad. Sci.*, 85:5879-5883 (1988); Mallender and Voss, *J. Biol. Chem.* 269:199-206 (1994); Ito and Kurosawa, *J. Biol Chem*, 27: 20668-20675 (1993), and; Gandecha et al., *Prot Express Purif.*, 5: 385-390 (1994).

The antibodies of this invention can be used for experimental purposes (e.g. localization of the HLA/peptide complexes, immunoprecipitations, Western Blots, flow cytometry, ELISA etc.) as well as diagnostic or therapeutic purposes, e.g., assaying extracts of tissue biopsies for the presence of HLA/peptide complexes, targeting delivery of cytotoxic or cytostatic substances to cells expressing the appropriate HLA/peptide complex. The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy. The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or antitumor agents, e.g., radioiodinated compounds, toxins such as ricin, methotrexate, cytostatic or cytolytic drugs, etc. Examples of diagnostic agents suitable for conjugating to the antibodies of this invention include e.g., barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-125, technitium-99m, iodine-131 and indium-111, nuclides for nuclear magnetic resonance such as fluorine and gadolinium. As used herein, "therapeutically useful agents" include any therapeutic molecule which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporin, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60. The antibodies may be administered to a subject having a pathological condition characterized by the presentation of the HLA/peptide complexes of this invention, e.g., melanoma and several other cancers, as described in Jungbluth et al., *Int. J. Cancer*, 92:856-860 (Jun 15 2001, incorporated herein by reference), in an amount sufficient to alleviate the symptoms associated with the pathological condition.

Soluble T cell receptors (sTCRs) which specifically bind to the HLA/peptide complexes described herein are also an aspect of this invention. In their soluble form T cell receptors are analogous to a monoclonal antibody in that they bind to HLA/peptide complex in a peptide-specific manner. Immobilized TCRs or antibodies may be used to identify and purify unknown peptide/HLA complexes which may be involved in cellular abnormalities. Methods for identifying and isolating sTCRs are known in the art, see for example WO 99/60119, WO 99/60120 (both incorporated herein by reference) which describe synthetic multivalent T cell receptor complex for binding to peptide-MHC complexes. Recombinant, refolded soluble T cell receptors are specifically described. Such receptors may be used for delivering therapeutic agents or detecting specific peptide-MHC complexes expressed by tumor cells. WO 02/088740 (incorporated by reference) describes a method for identifying a substance that binds to a peptide-MHC complex. A peptide-MHC complex is formed between a predetermined MHC and peptide known to bind to such predetermined MHC. The complex is then use to screen or select an entity that binds to the peptide-MHC complex such as a T cell receptor. The method could also be applied to the selection of monoclonal antibodies that bind to the pre-determined peptide-MHC complex.

Also an embodiment of this invention are nucleic acid molecules encoding the antibodies and T cell receptors of this invention and host cells, e.g., human T cells, transformed with a nucleic acid molecule encoding a recombinant antibody or antibody fragment, e.g., scFv or Fab, or a TCR specific for a pre-designated HLA/peptide complex as described herein. Recombinant Fab or TCR specific for a pre-designated HLA/peptide complex in T cells have been described in, e.g., Willemsen et al., "A phage display selected fab fragment with MHC class I-restricted specificity for MAGE-A1 allows for retargeting of primary human T lymphocytes" *Gene Ther.* 2001 Nov;8(21):1601-8. PMID: 11894998 [PubMed—indexed for MEDLINE] and Willemsen et al., "Grafting primary human T lymphocytes with cancer-specific chimeric single chain and two chain TCR". Gene Ther. 2000 Aug;7 (16):1369-77. PMID: 10981663 [PubMed—indexed for MEDLINE] (both incorporated herein by reference) and have applications in an autologous T cell transfer setting. The autologous T cells, transduced to express recombinant antibody or sTCR, may be infused into a patient having an pathological condition associated with cells expressing the HLA/peptide complex. The transduced T cells are administered in an amount sufficient to inhibit the progression or alleviate at least some of the symptoms associated with the pathological condition.

An embodiment of this invention is a method for promoting regression or inhibiting progression of a tumor in a subject in need thereof wherein the tumor expresses a complex of HLA and peptide. The method comprises administering an antibody, antibody fragment or soluble T cell receptor, which specifically binds to the HLA/peptide complex, or by administering cells transduced so that they express those antibodies or TcR in amounts that are sufficient to promote the regression or inhibit progression of the tumor expressing the HLA/peptide complex, e.g., a melanoma or other cancer. The antibodies, antibody fragments and soluble T cell receptors may be conjugated with, or administered in conjunction with, an antineoplastic agent, e.g., radioiodinated compounds, toxins such as ricin, methotrexate, or a cytostatic or cytolytic agent as discussed supra. See e.g., Patan et al., *Biochem. Biophys. Acta*, 133:C1-C6 (1997), Lode et al., *Innunol. Res.*, 21:279-288 (2000) and Wihoff et al., *Curr. Opin. Mo. Ther.*, 3:53-62 (2001) (all incorporated herein by reference) for a discussion of the construction of recombinant immunotoxins, antibody fusions with cytokine molecules and bispecific antibody therapy or immunogene therapy.

The invention also embraces functional variants of the HLA class I binding peptide. As used herein, a "functional variant" or "variant" of a an HLA class I binding peptide is a peptide which contains one or more modifications to the primary amino acid sequence of the HLA class I binding peptide and retains the HLA class I and T cell receptor binding properties disclosed herein. Modifications which create the HLA class I binding peptide functional variant can be made for example 1) to enhance a property of the HLA class I binding peptide, such as peptide stability in an expression system or the stability of protein-protein binding such as HLA-peptide binding; 2) to provide a novel activity or property to the HLA class I binding peptide, such as addition of an antigenic epitope or addition of a detectable moiety; or 3) to provide a different amino acid sequence that produces the same or similar T cell stimulatory properties. Modifications to the HLA class I binding peptide can be made to a nucleic acid which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Modifications also embrace fusion proteins comprising all of part of the MAGEA2, A3, A6, or A12 HLA class I binding peptide amino acid sequence.

The amino acid sequence of the HLA class I binding peptides may be of natural or non-natural origin, that is, they may comprise a natural HLA class I binding peptide molecule or may comprise a modified sequence as long as the amino acid sequence retains the ability to stimulate T cells when presented and retains the property of binding to an HLA class I molecule such as an HLA-Cw*07 molecule. For example, HLA class I binding peptides in this context may be fusion proteins of a HLA class I binding peptide and unrelated amino acid sequences, a synthetic peptide of amino acid sequences shown in SEQ ID NO: 1 or the sequence consisting of amino acids 6-14 of SEQ ID NO: 1, labeled peptides, peptides isolated from patients with a cancer expressing a molecule which comprises the peptides, peptides isolated from cultured cells which express such a molecule, peptides coupled to nonpeptide molecules (for example in certain drug delivery systems) and other molecules which include the amino acid sequence of consisting of amino acids 6-14 of SEQ ID NO: 1.

Preferably, the HLA class I binding peptides are non-hydrolyzable. To provide such peptides, one may select HLA class I binding peptides from a library of non-hydrolyzable peptides, such as peptides containing one or more D-amino acids or peptides containing one or more non-hydrolyzable peptide bonds linking amino acids. Many non-hydrolyzable peptide bonds are known in the art, along with procedures for synthesis of peptides containing such bonds. Non-hydrolyzable bonds include -psi[Ch.sub.2 NH]-reduced amide peptide bonds, -psi[COCH.sub.2]-ketomethylene peptide bonds, -psi [CH(CN)NH]-(cyanomethlyene) amino peptide bonds, -psi [CH.sub.2CH(OH)]-hydroxyethylene peptide bonds, -psi [CH.sub.2 O]-peptide bonds, and -psi[CH.sub.2 S]-thiomethylene peptide bonds. Methods for determining such functional variants are provided in U.S. Pat. No. 6,087,441, incorporated by reference.

If a variant involves a change to an amino acid of SEQ ID NO: 1 or the sequence described supra, functional variants of the HLA class I binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Methods for identifying functional variants of the HLA class I binding peptides are provided in U.S. Pat. Nos. 6,277,956 and 6,326,200 and published PCT application WO0136453 (U.S. patent application Ser. Nos. 09/440,621, 09/514,036, 09/676,005), all of which are incorporated by reference.

Thus methods for identifying functional variants of an HLA class I binding peptide are provided. In general, the methods include selecting an HLA class I binding peptide, an HLA class I binding molecule which binds the HLA class I binding peptide, and a T cell which is stimulated by the HLA class I binding peptide presented by the HLA class I binding molecule. In preferred embodiments, the HLA class I binding peptide comprises the amino acid sequence of amino acids 6-14 of SEQ ID NO: 1. More preferably, the peptide consists of amino acids 6-14 of SEQ ID NO: 1. A first amino acid residue of the HLA class I binding peptide is mutated to prepare a variant peptide. Any method for preparing variant peptides can be employed, such as synthesis of the variant peptide, recombinantly producing the variant peptide using a mutated nucleic acid molecule, and the like.

The binding of the variant peptide to HLA class I binding molecule and stimulation of the T cell are then determined according to standard procedures wherein binding of the variant peptide to the HLA class I binding molecule and stimulation of the T cell by the variant peptide presented by the HLA class I binding molecule indicates that the variant peptide is a functional variant. For example, the variant peptide can be contacted with an antigen presenting cell which contains the HLA class I molecule which binds the MAGE-3 peptide to form a complex of the variant peptide and antigen presenting cell. This complex can then be contacted with a T cell which recognizes the epitope formed by the HLA class I binding peptide and the HLA class I binding molecule. T cells can be obtained from a patient having a condition characterized by expression of a molecule which comprises the peptide referred to supra, such as MAGEA2, MAGEA3, MAGEA6, or MAGEA12. Recognition of variant peptides by the T cells can be determined by measuring an indicator of T cell stimulation.

Binding of the variant peptide to the HLA class I binding molecule and stimulation of the T cell by the epitope presented by the complex of variant peptide and HLA class I binding molecule indicates that the variant peptide is a functional variant. The methods also can include the step of comparing the stimulation of the T cell by the epitope formed by the HLA class I binding peptide and the HLA class I molecule, stimulation of the T cell as a determination of the effectiveness of the stimulation of the T cell by the epitope. By comparing the epitope involving the peptide formed by the functional variant with the HLA class I binding peptide, peptides which are functional variants with increased T cell stimulatory properties can be prepared.

Variants of the HLA class I binding peptides prepared by any of the foregoing methods can be sequenced, if necessary, to determine the amino acid sequence and thus deduce the nucleotide sequence which encodes such variants.

Other features of the invention will be clear to the skilled artisan, and need not be reiterated herein.

We Claim:

1. An isolated peptide consisting of the amino acid sequence set forth in SEQ ID NO: 1.

2. An isolated peptide consisting of the amino acid sequence set forth in SEQ ID NO: 2.

3. An isolated peptide consisting of amino acids 6-14 of SEQ ID NO: 1, and an additional 5-10 amino acids which are concatenated to amino acid 6 or amino acid 14 of SEQ ID NO: 1, wherein said additional 5-10 amino acids are identical to amino acids which immediately precede amino acid 6 or immediately follow amino acid 14 in a MAGE-A2, MAGE-A3, MAGE-A6, or MAGE-A12 molecule.

4. An isolated peptide consisting of amino acids 6-14 of SEQ ID NO: 1, and additional 1-6 amino acids which are concatenated to amino acid 6 or amino acid 14 of SEQ ID NO: 1, wherein said additional 1-6 amino acids are identical to amino acids which immediately precede amino acid 6 or immediately follow amino acid 14 in a MAGE-A2, MAGE-A3, MAGE-A6, or MAGE-A12 molecule.

* * * * *